(12) United States Patent
Chao

(10) Patent No.: US 8,439,943 B2
(45) Date of Patent: May 14, 2013

(54) TOURNIQUET

(75) Inventor: Chia-Chang Chao, Taipei (TW)

(73) Assignee: Huntex Corporation, Taipei (TW)

( * ) Notice: Subject to any disclaimer, the term of this patent is extended or adjusted under 35 U.S.C. 154(b) by 417 days.

(21) Appl. No.: 12/477,135

(22) Filed: Jun. 3, 2009

(65) Prior Publication Data
US 2010/0312271 A1 Dec. 9, 2010

(51) Int. Cl.
- *A61B 17/00* (2006.01)
- *A44B 1/04* (2006.01)
- *A44B 11/12* (2006.01)
- *A44B 11/25* (2006.01)
- *A44B 17/00* (2006.01)
- *B68B 5/00* (2006.01)
- *A41F 1/00* (2006.01)
- *A43C 11/00* (2006.01)

(52) U.S. Cl.
USPC .................. 606/203; 24/170; 24/614

(58) Field of Classification Search ..... 606/203; 24/168, 24/170, 191, 193, 614, 615, 641
See application file for complete search history.

(56) References Cited

U.S. PATENT DOCUMENTS

| | | | | |
|---|---|---|---|---|
| 4,102,343 A | * | 7/1978 | Schneider | 606/203 |
| 4,125,115 A | * | 11/1978 | Mayo et al. | 606/203 |
| 4,211,289 A | * | 7/1980 | Klein | 600/499 |
| 4,243,039 A | * | 1/1981 | Aginsky | 606/203 |
| 4,516,576 A | * | 5/1985 | Kirchner | 606/203 |
| 4,526,165 A | * | 7/1985 | Mielnik et al. | 128/882 |
| 4,561,437 A | * | 12/1985 | Kirchner | 606/203 |
| 5,314,437 A | * | 5/1994 | Holtsch | 606/157 |
| 5,535,485 A | * | 7/1996 | Kirchner | 24/170 |
| 5,749,127 A | * | 5/1998 | Hsieh | 24/3.13 |
| 6,217,601 B1 | * | 4/2001 | Chao | 606/203 |
| 6,884,254 B2 | * | 4/2005 | Brooks | 606/201 |
| 7,370,392 B2 | * | 5/2008 | Holtsch | 24/170 |
| 7,468,067 B2 | * | 12/2008 | Licata et al. | 606/203 |
| 7,582,102 B2 | * | 9/2009 | Heinz et al. | 606/203 |
| 7,947,061 B1 | * | 5/2011 | Reis | 606/203 |

FOREIGN PATENT DOCUMENTS

| TW | 395234 | 6/2000 |
|---|---|---|
| TW | M263082 | 5/2005 |

* cited by examiner

*Primary Examiner* — Gary Jackson
*Assistant Examiner* — Amy Shipley
(74) *Attorney, Agent, or Firm* — Muncy, Geissler, Olds & Lowe, PLLC

(57) ABSTRACT

A tourniquet includes a first and a second elements and a strap having one end winding around a human body and threading through the first element. The first element has a latch slot and a latch element. The second element has a coupling element at one end latchable with the latch element and the other end fastened to the strap. The first element has an upper and a lower cases and a brake unit inside. The upper and lower cases have respectively an upper and a lower openings threaded through by the strap. The brake unit has a detent edge at one end and an axle at the other end extended to form an actuating member movable with the brake unit about the axle, and an elastic element provides a force for the detent edge to butt the strap from the upper opening to the lower opening.

9 Claims, 7 Drawing Sheets

TOURNIQUET

FIELD OF THE INVENTION

The present invention relates to a tourniquet that is loose-proof and detachable quickly.

BACKGROUND OF THE INVENTION

Tourniquet is a useful medical item to provide contracting pressure to stop local hemorrhage in a human body and also aid intravenous injection or blood drawing. Its principle is to compress veins by contracting the limbs so that the diameters of veins are shrunk smaller to hinder blood from flowing back to the heart. The obstructed blood is held in the veins and inflates the veins so that the veins are noticeable beneath the skin to facilitate fast and precise recognition to make injection or blood drawing smoother. Thus it keeps patients from discomfort caused by repetitive needling and also reduces the risk of infection.

The conventional tourniquet is a small and elongate rubber tube directly bound on a selected portion of the human body. Its small size makes binding strength difficult to control. It easily results in too much binding force and friction that make patients uncomfortable and injure the patients who have delicate skin. Rapid bouncing often occurs during unfastening that generates a great elastic returning force which might cause additional injury to patients' delicate skin. Moreover, adjusting the binding portion involves tedious repetitive unfastening and binding processes. In emergency situations such as injections are required for a great number of patients, it causes a lot of trouble for medical staff. To remedy the aforesaid problems, many improvements have been proposed in prior art. For instance, R.O.C. Patent No. M263082 entitled "Tourniquet" has a latch element coupling with a connector, a circular strap threading through the connector, and a transverse bar in the connector to form tightening of the strap. The flattened strap alleviates uncomfortable feeling of the patients caused by friction or stretching of the skin. However, as the strap winds around the cylindrical transverse bar, the strap easily slides and loosens due to the cylindrical shape. It is also difficult to fine adjust the contraction fore due to the structure of the transverse bar. The latch element and the connector also are jutting from patient's body after latched rather than positioned flatly and snuggly on patient's limbs and prone to be hit by external objects. This results in a risk of loosening the tourniquet. In environments where dust or sands are abundant, the dust or sands could scatter between the transverse bar and the strap and result in anchoring failure and loss of binding force. R.O.C. patent No. 395234 entitled "Controllable tourniquet" submitted by the Applicant provides a latch seat coupling with a connector and an elastic and circular strap to tightly binding the limbs of an user. Instead of using the transverse bar previously discussed to provide an anchoring force, a teeth surface on one end is provided to clamp the elastic strap to form a secure coupling. The coupling force is not affected by dust or sands. But it still has a deficiency by not flatly in contact with the limbs of patients, and is prone to be hit by external objects. Moreover, anchor operation by coupling the teeth surface and the elastic strap is tedious; hence it still leaves a lot to be desired.

Therefore there are still rooms for improvement on the conventional tourniquets. To develop a tourniquet that provides fast adjustment of tightening and loosening, and offers a simpler structure to reduce production cost, and is unaffected by dust or sands is still a need remained to date.

SUMMARY OF THE INVENTION

In view of the deficiency of the conventional tourniquets, the primary object of the present invention is to provide a tourniquet to form contracting forces unaffected by dust or sands and offer faster and easier adjustment of loosening and tightening, and a simpler structure to overcome the problems of the conventional tourniquets.

To achieve the foregoing object, the tourniquet according to the invention includes a first element, a second element and a strap winding around a human body with one end threading through the first element. It also has features as follow: the first element has one end with a latch slot and at least one latch element located thereon. The second element also has one end with a coupling element coupled with the latch element and the other end fastened to one end of the strap. The first element has an upper case and a lower case and a brake unit located between the upper and lower case. The upper and lower cases further have respectively an upper opening and a lower opening threaded through by the strap. The brake unit has one end with a detent edge formed thereon to butt the strap, and the other end connected to the axle pivotally coupled on the first element one end where the axle located is extended to form an actuating member which is movable with the brake unit about the axle between the upper and lower cases. The first element also has a detaching button and a release button movable respectively with the latch element and the actuating member. The brake unit may also include an elastic element to provide a desired force for the detent edge to butt the strap through the direction from the upper opening to the lower opening. The strap is wound from the second element to the lower opening and threads through a pad.

By means of the construction set forth above, the invention provides many benefits over the conventional techniques, notably:

1. With the brake unit displacing the conventional transverse bar to anchor the strap, loosening due to deficient of friction force caused by smearing of the dust or sands can be prevented, and the tourniquet is more reliable when in use.

2. With the detaching and release buttons located at noticeable locations where the force is easy to be applied and thus facilitate the use of the tourniquet. Detachment and release can be accomplished quickly. Adjustment of loosening and tightening can also be performed faster through the brake unit.

3. By coupling the first and second elements, the tourniquet can be wound and positioned on a patient's limb in a flat and snug manner without jutting outwards. The possibility of loosening caused by mistaken touching or inadvertent hitting can be reduced.

4. While the strap provides a greater portion of contracting force, the pad also provides a concentrated compression force to enhance one-way or single-point compression to improve hemorrhage stopping effect and stability.

The foregoing, as well as additional objects, features and advantages of the invention will be more readily apparent from the following detailed description, which proceeds with reference to the accompanying drawings.

DETAILED DESCRIPTION OF THE PREFERRED EMBODIMENTS

Figure 1:
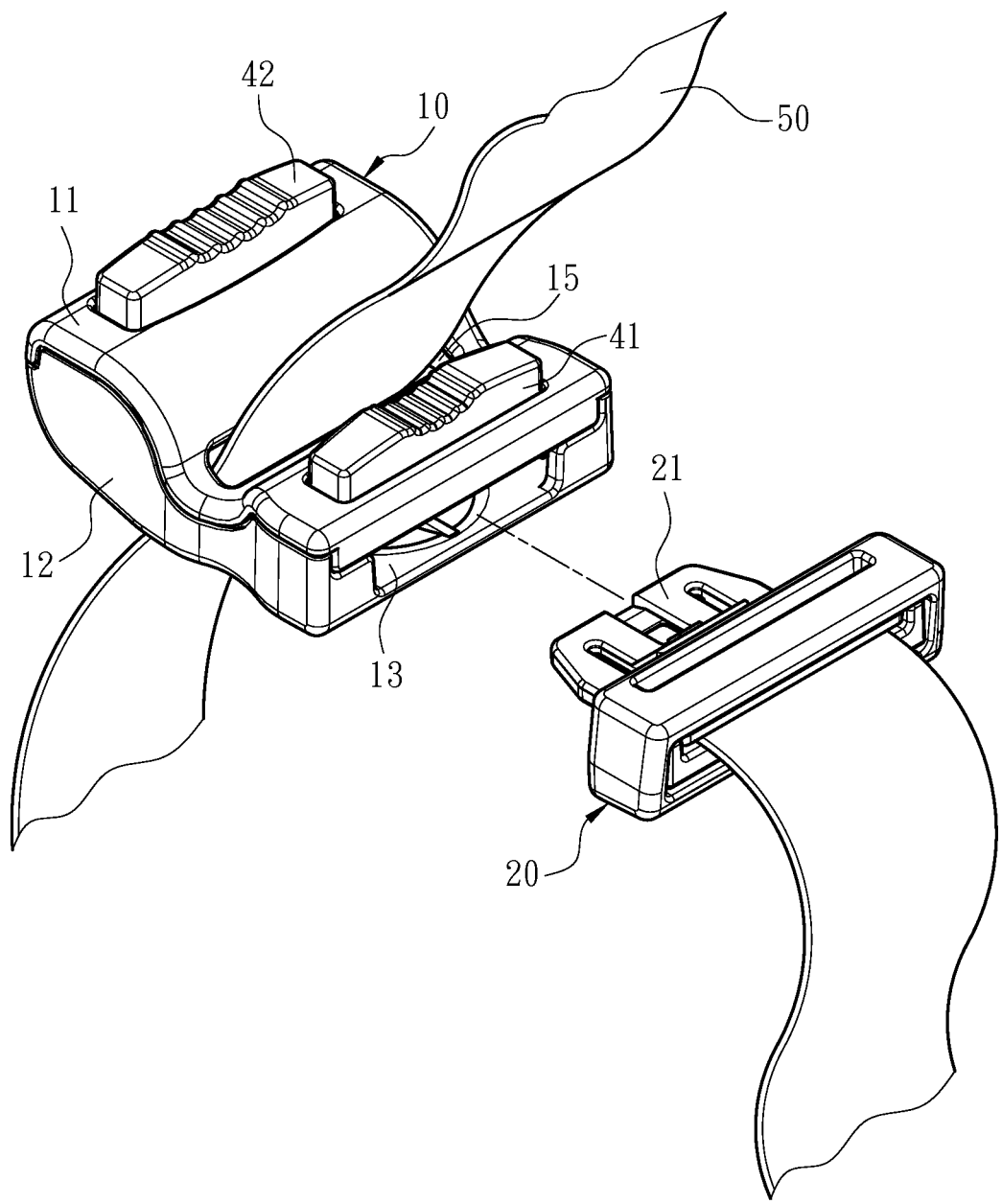
FIG. 1 is a perspective view of the invention.
Figure 2:
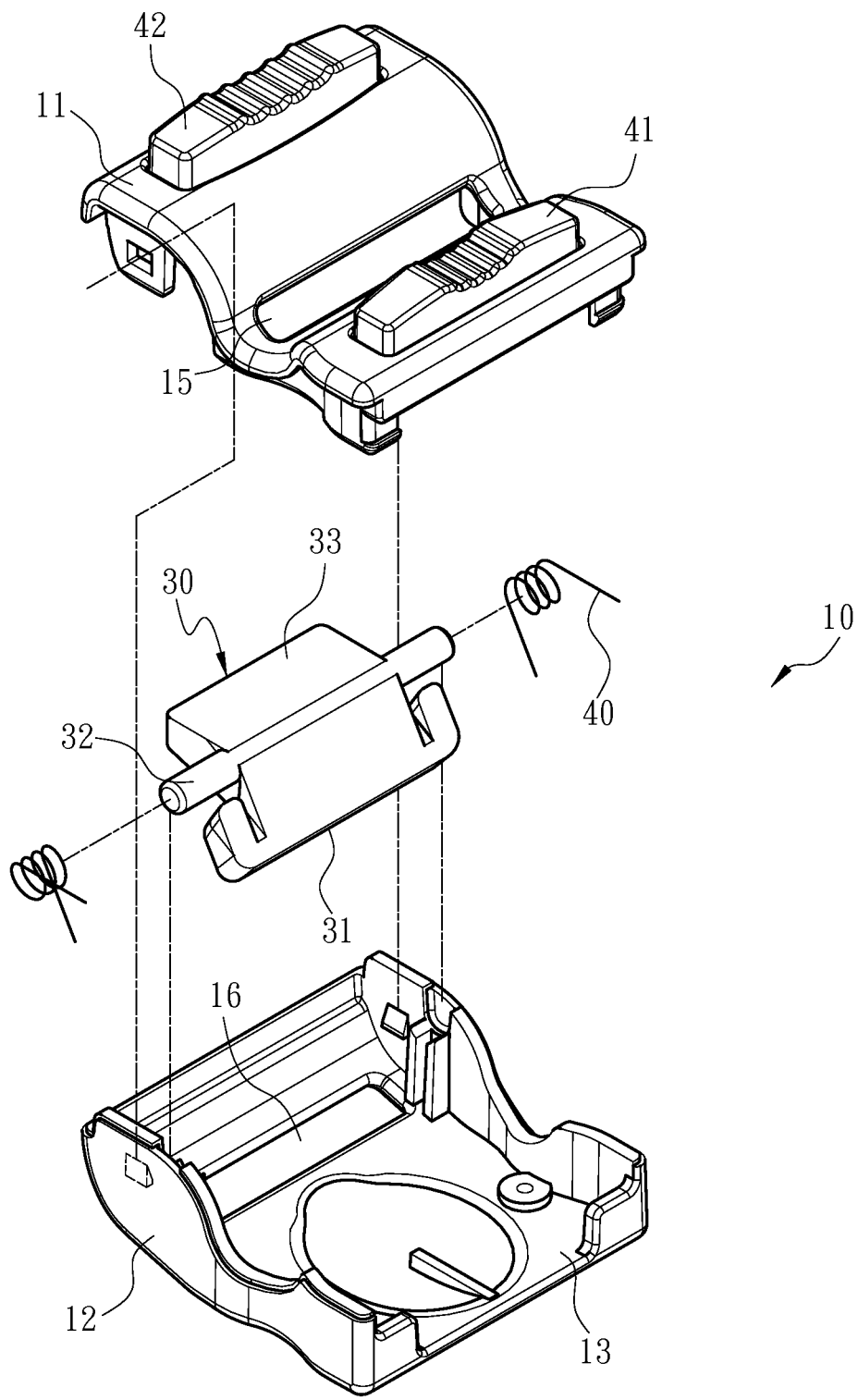
FIG. 2 is an exploded view of the first element of the invention.
Figure 3A:
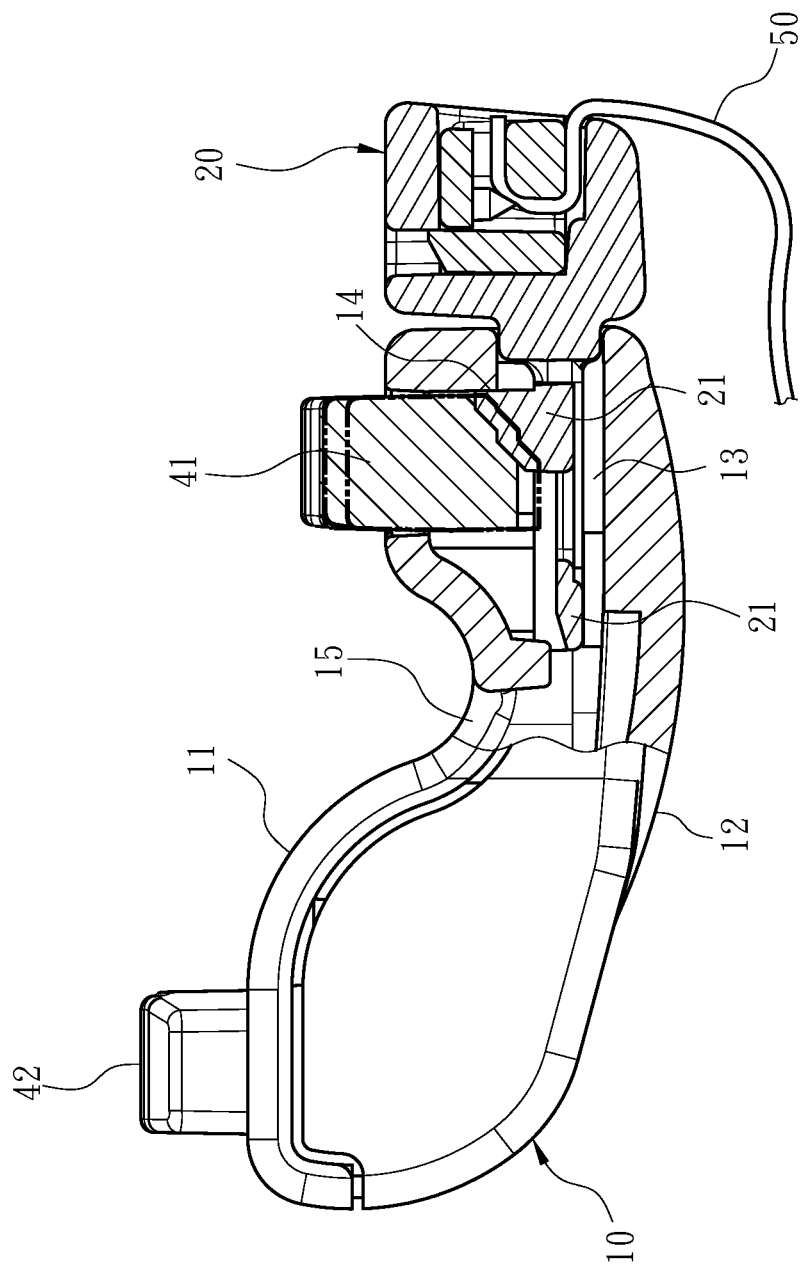
FIGS. 3A and 3B are sectional views of the first and second elements of the invention in operating conditions.
Figure 4:
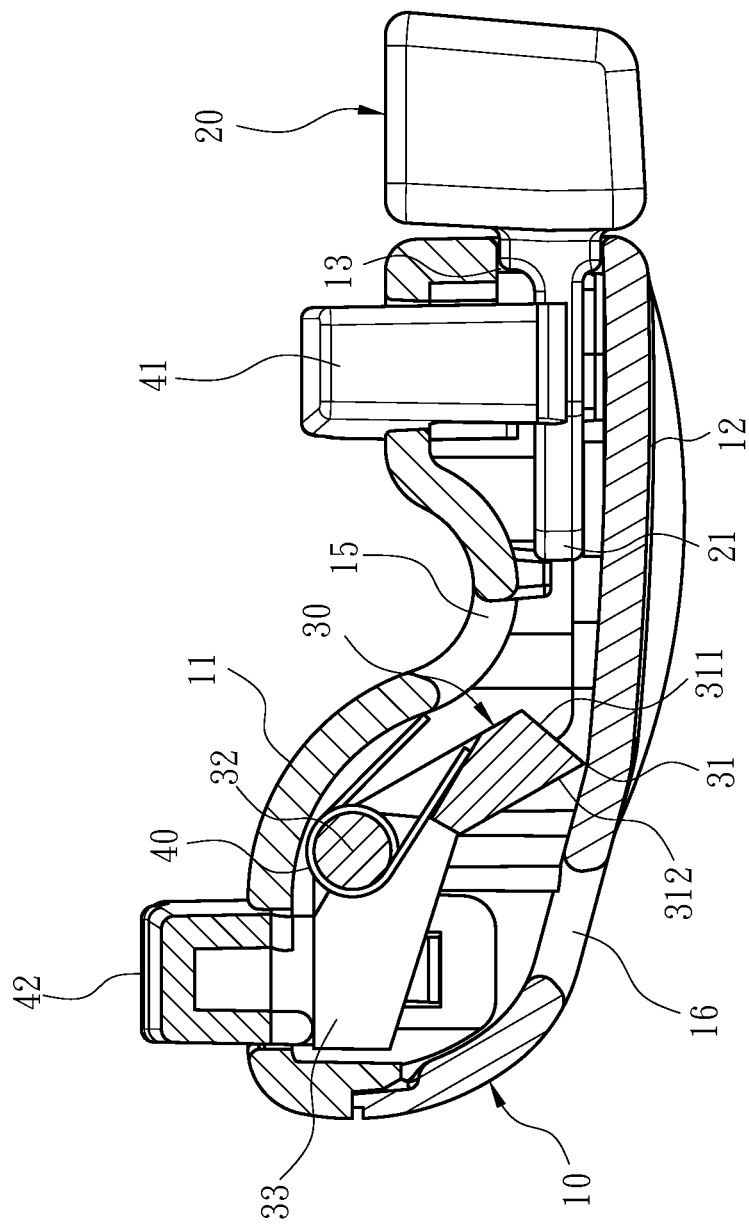
FIG. 4 is a sectional view of the first element of the invention.

Please refer to FIGS. 1, 2 and 4, the basic structure of the invention includes a first element 10, a second element 20 and a strap 50 winding around a human body with one end threading through the first element 10. The first element 10 has one end with a latch slot 13 formed thereon and at least one latch element 14 located therein (referring to FIG. 3A). The second element 20 has one end with a coupling element 21 located thereon to couple with the latch element 14 and the other end fastened to one end of the strap 50. The first element 10 also has an upper case 11, a lower case 12 and a brake unit 30 located between the upper case 11 and the lower case 12. The upper and lower cases 11 and 12 have respectively an upper opening 15 and a lower opening 16 threaded through by the strap 50. The brake unit 30 has one end formed a detent edge 31 to butt the strap 50 and the other end with an axle 32 formed thereon and pivotally coupled on the first element 10. One end where the axle 32 is located also is extended to form an actuating member 33 which is movable with the brake unit 30 about the axle 32 between the upper and lower cases 11 and 12. The first element 10 further has a detaching button 41 movable with the latch element 14 and a release button 42 movable with the actuating member 33.

Figure 3B:
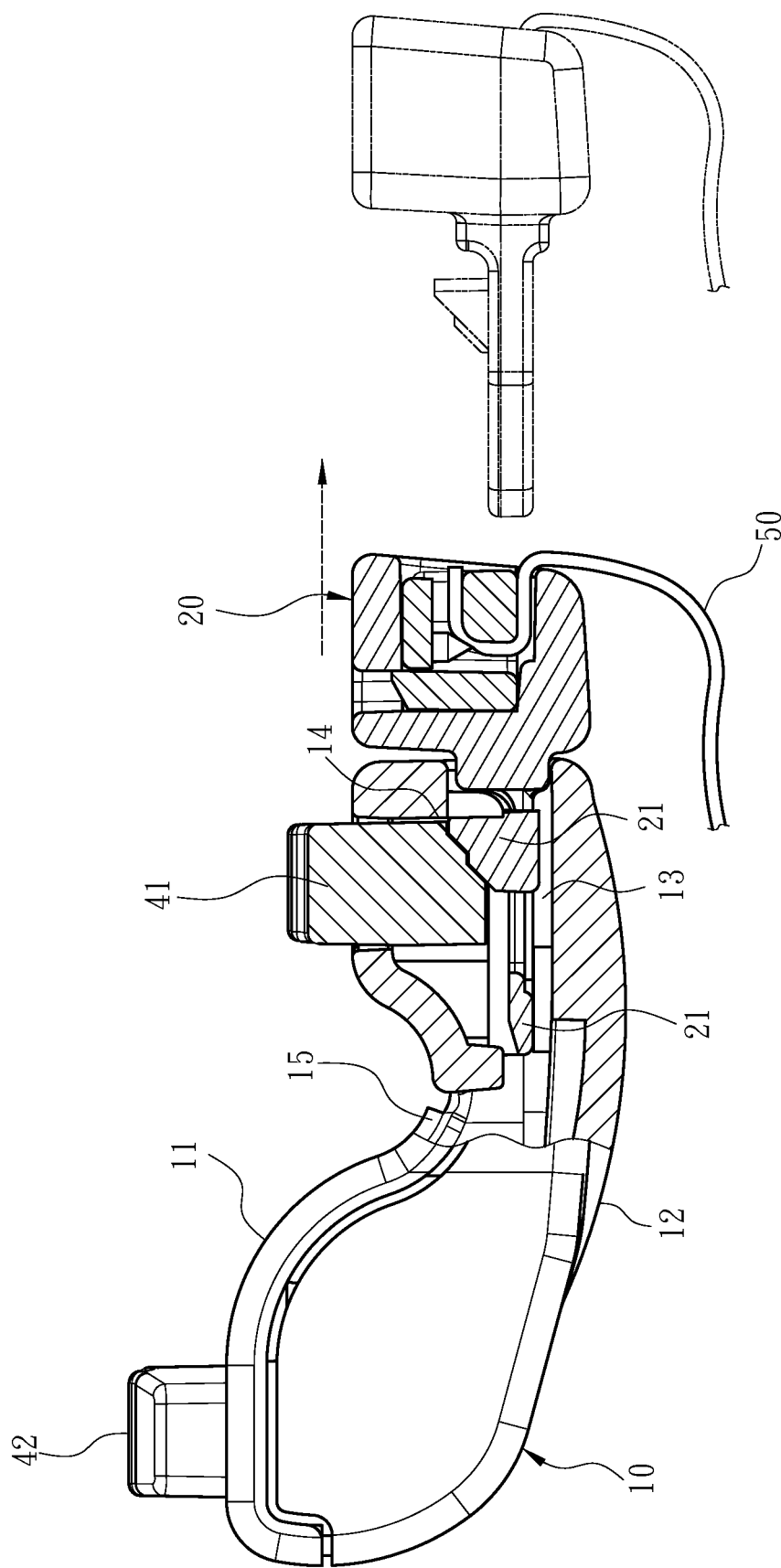
Figure 5A:
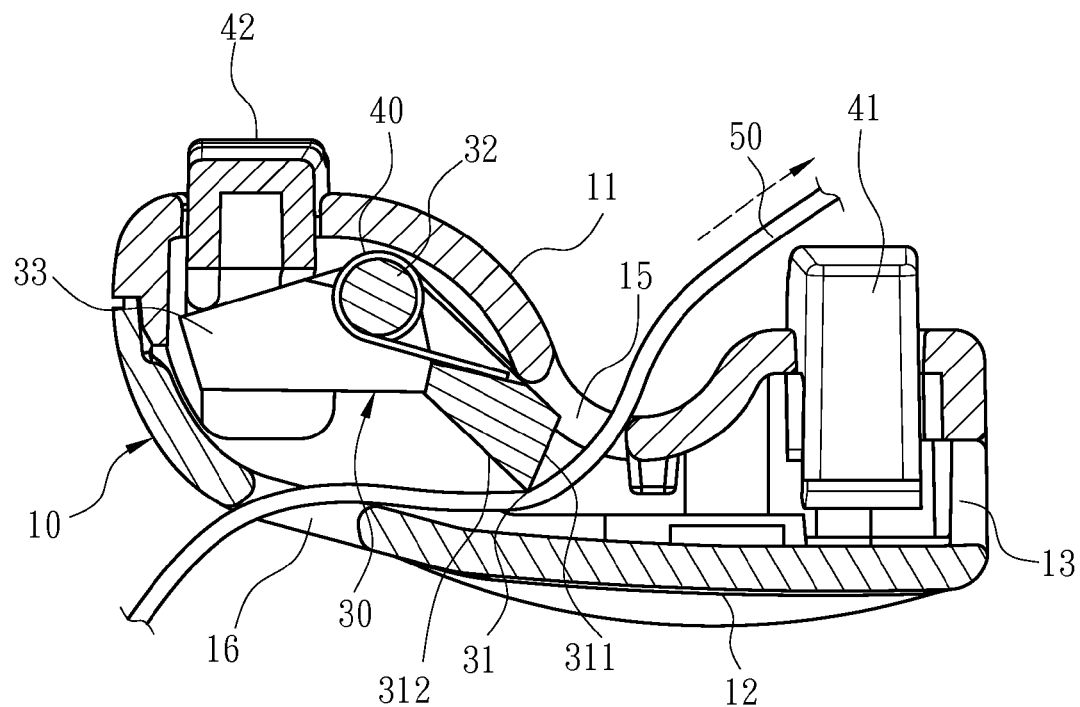
FIGS. 5A and 5B are schematic views of operating conditions of the strap in the first element.
Figure 5B:
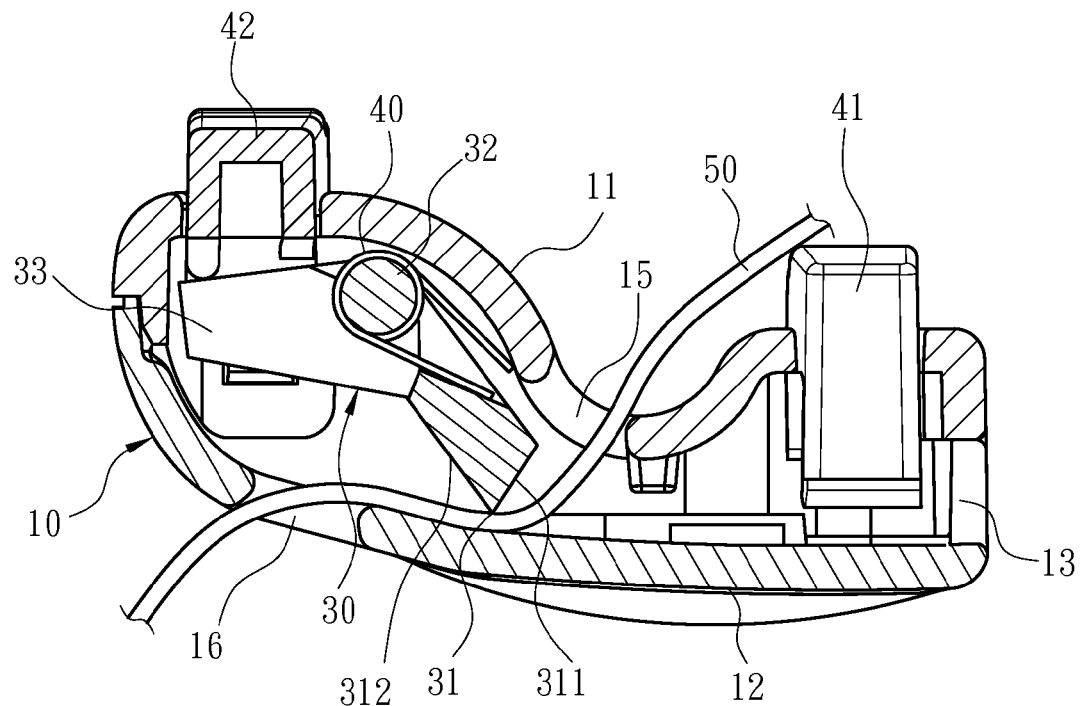
Figure 6:
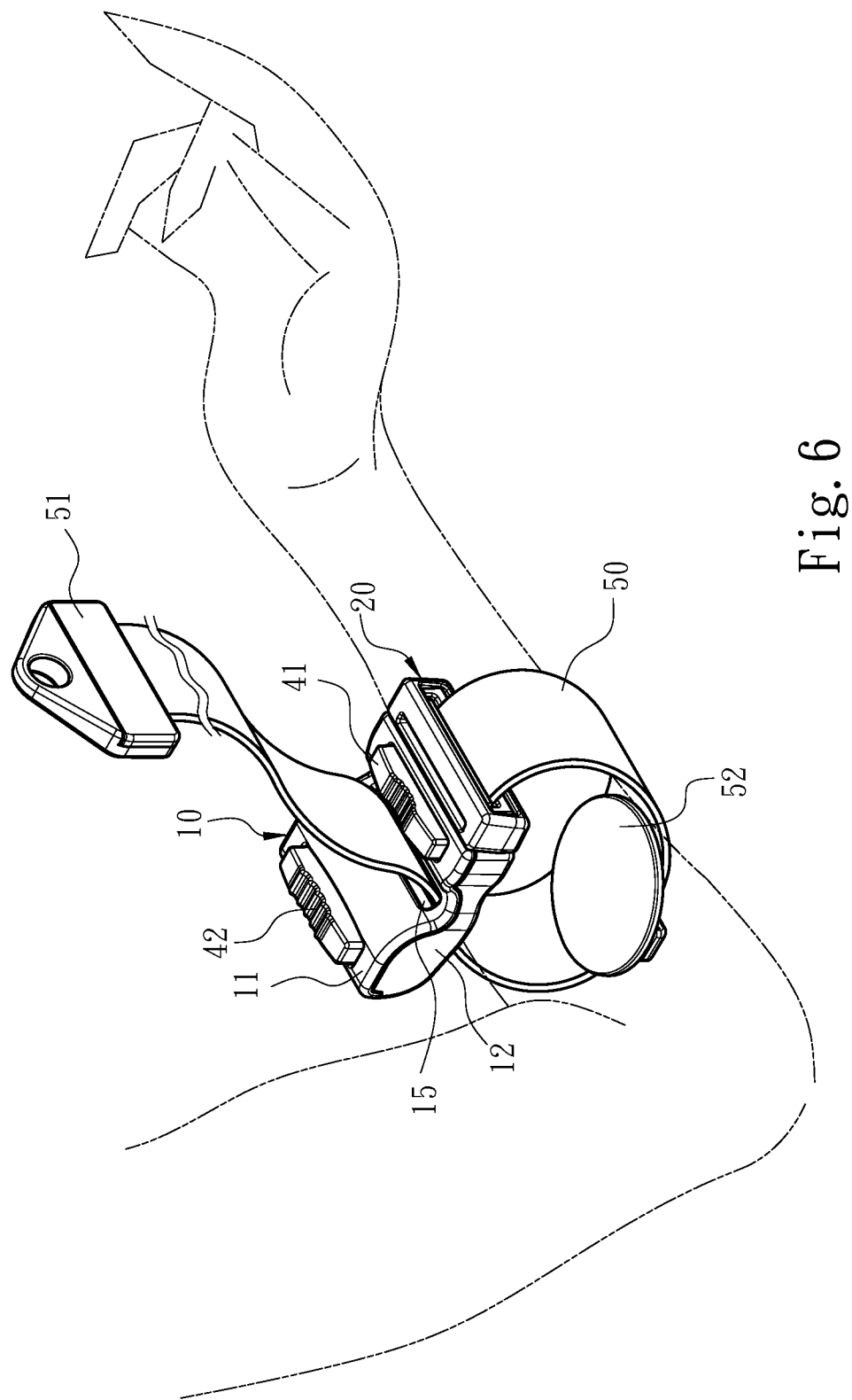
FIG. 6 is a schematic view of an embodiment of the invention.

Also refer to FIGS. 3A and 3B for coupling and separation of the first and second elements 10 and 20. In an embodiment shown in the drawings, when the coupling element 21 latches with the latch element 14 through the latch slot 13, the detaching button 41 is bounced upwards by the coupling element 21 through mutual contact sloped surfaces formed thereon. When there is a desire to separate the first and second elements 10 and 20, depress the detaching button 41 to butt the coupling element 21, the coupling element 21, due to the elasticity of its inherent material characteristics, moves slightly away from the latch element 14 so that the second element 20 can separate from the first element 10. While the latching method of the first and second elements 10 and 20 previously discussed is not the limitation of the invention. Other latching means and methods may also be adopted. Refer to FIGS. 5A and 5B for positioning of the strap 50. The brake unit 30 has an elastic element 40 to provide a force for the detent edge 31 to butt the strap 50 through the direction from the upper opening 15 to the lower opening 16 against the lower case 12. In the preferred embodiment shown in the drawings, the elastic element 40 encompasses the axle 32 and has one end butting the brake unit 30 and the other end butting an inner wall of the upper case 11. The elastic element 40 provides a pressure to push the brake unit 30 against the inner wall of the upper case 11 so that the detent edge 31 can butt the strap 50 against an inner wall of the lower case 12. The detent edge 31 has a first plane 311 and a second plane 312. The first and second planes 311 and 312 may be a plurality of concave surfaces and the detent edge 31 is formed with triangular saw-toothed edges, concave-arched saw-toothed edges or convex-arched saw-toothed edges to enhance gripping and positioning forces while the strap 50 is butted against the lower case 12. Also refer to FIG. 6 for a preferred embodiment of the invention. The strap 50 has one end fastened to the second element 20. After having wound around a desired portion, one end of the strap 50 is threaded through the lower opening 16 and thread out the upper opening 15, then the strap 50 is tightly contracted. Movement of the strap 50 in the first element 10 will be discussed later. The one end of the strap 50 threading through the upper opening 15 may be coupled to a retaining element 51 greater than the upper opening 15 to prevent the strap 50 from escaping the first element 10 during unfastening, so that the inconvenience of redoing threading through the first element 10 can be avoided. The strap 50 may also be coupled with a pad 52 on a spot in contact with the human body to provide uniform force applying on the human body without skewing. After the first and second elements 10 and 20 are coupled by latching of the coupling element 21 and the latch element 14 through the latch slot 13, the strap 50 forms a closed path. Depress the detaching button 41 can quickly unfasten the first and second elements 10 and 20. This is because the detaching button 41 pushes the coupling element 21 to escape from the latch element 14 so that the first and second elements 10 and 20 can be separated. The mating latch relationship between the latch element 14 and the coupling element 21 may be changed as required to provide more versatility without being confined to the one previously discussed.

Referring to FIGS. 5A and 5B, after the strap 50 has been threaded through the upper opening 15 and lower opening 16 through the first element 10, the force applied to the strap 50 through the upper opening 15 also is transmitted to the detent edge 31 in tight contact with the strap 50. The brake unit 30 also receives the force directing towards the upper opening 15, and the brake unit 30 compresses the elastic element 40 to lean against the inner wall of the upper case 11 so that the strap 50 is no longer clamped between the detent edge 31 and the lower case 12, therefore the strap 50 can be freely drawn out from the upper opening 15. As the brake unit 30 is leaned against the inner wall of the upper case 11, it enables the deviation of the detent edge 31, during movement of the strap 50, it is easily in contact with the second plane 312 and continuously provides the butting force for the brake unit 30 against the inner wall of the upper case 11 via the second plane 312 and the detent edge 31. Referring to FIG. 5B, when the force to draw the strap 50 through the upper opening 15 is stopped, the force of compressing the elastic element 40 from the brake unit 30 is released so that the brake unit 30 returns to its original position. The strap 50 is tightly clamped between the detent edged 31 and the inner wall of the lower case 12. On the contrary, trying to draw out the strap 50 through the lower opening 16 will push the first plane 311 so that the detent edge 31 can further press the strap 50, as a result. The strap 50 is anchored more firmly without moving. Depressing the release button 42, then the actuating member 33 is pushed and the brake unit 30 is moved against the inner wall of the upper case 11 again, the strap 50 is no longer clamped between the detent edge 31 and the lower case 11 and is in a loose condition. By means of the structure previously discussed, the strap 50 can be tightly contracted without loosening. The detent edge 31 can enhance the anchoring force and is more reliable than the conventional transverse bar.

While the preferred embodiments of the invention have been set forth for the purpose of disclosure, modifications of the disclosed embodiments of the invention as well as other embodiments thereof may occur to those skilled in the art. Accordingly, the appended claims are intended to cover all embodiments which do not depart from the spirit and scope of the invention.

What is claimed is:

1. A tourniquet, comprising:

a strap;

a first element including an upper case, a lower case coupled with the upper case, a cavity formed between the upper case and the lower case and a brake unit pivotally mounted in the cavity between the upper case and the lower case by an axle, the upper and lower cases being coupled with each other to form a latch slot holding at least one latch element, the upper case including a release button at one side thereof located above the brake unit for triggering the brake unit and the upper case including a detaching button at another side thereof, the detaching button being located above the latch element for triggering the latch element, and an upper opening between the release button and the detaching button being threaded through by one end of the strap, the lower case including a lower opening corresponding to the upper opening and being threaded through by the strap; the brake unit having a detent edge extending from one side of the axle to butt the strap and an actuating member extended from another side of the axle to be driven by the release button, the axle including two ends respectively coupled by an elastic element to drive the brake unit movably about the axle between the upper case and the lower case and to drive the detent edge to butt the strap through the direction from the upper opening towards the lower opening against the lower case; and a second element which is fastened to the strap including a coupling element latchable with the latch element of the first element.

2. The tourniquet of claim 1, wherein the detent edge has a first plane and a second plane.

3. The tourniquet of claim 2, wherein the first plane and the second planes are formed in a plurality of concave surfaces, the detent edge having triangular saw-toothed edges, concave-arched saw-toothed edges or convex-arched saw-toothed edges.

4. The tourniquet of claim 3, wherein one end of the strap threading through the first element is fastened to a retaining element greater than the upper opening.

5. The tourniquet of claim 4, wherein the strap winding to the lower opening through the second element threads through a pad.

6. The tourniquet of claim 1, wherein the brake unit is contained within the upper and lower cases.

7. The tourniquet of claim 1, wherein the lower opening is on a side of the first element opposite the upper opening such that the upper opening is on a top of the first element and the lower opening is on a bottom of the first element and wherein the latch slot is on a side of the first element between the top and the bottom of the first element.

8. The tourniquet of claim 1, wherein the strap extends from a top and bottom of the first element.

9. The tourniquet of claim 1, wherein the release button interfaces with the brake element so that depressing the release button causes the tension on the strap to be released.

* * * * *